US010617615B2

(12) United States Patent
Murray et al.

(10) Patent No.: US 10,617,615 B2
(45) Date of Patent: Apr. 14, 2020

(54) METHOD OF TREATING HAIR

(71) Applicant: Conopco, Inc., Englewood Cliffs, NJ (US)

(72) Inventors: Andrew Malcolm Murray, Parkgate (GB); Prem Kumar Cheyalazhagan Paul, Wirral (GB)

(73) Assignee: CONOPCO, INC., Englewood Cliffs, NJ (US)

( * ) Notice: Subject to any disclaimer, the term of this patent is extended or adjusted under 35 U.S.C. 154(b) by 527 days.

(21) Appl. No.: 15/036,429

(22) PCT Filed: Nov. 19, 2014

(86) PCT No.: PCT/EP2014/074998
§ 371 (c)(1),
(2) Date: May 13, 2016

(87) PCT Pub. No.: WO2015/075062
PCT Pub. Date: May 28, 2015

(65) Prior Publication Data
US 2016/0287496 A1 Oct. 6, 2016

(30) Foreign Application Priority Data

Nov. 21, 2013 (EP) ..................................... 13193935

(51) Int. Cl.
*A61Q 5/06* (2006.01)
*A61K 8/365* (2006.01)
*A61K 8/362* (2006.01)
*A45D 7/04* (2006.01)

(52) U.S. Cl.
CPC ................ *A61K 8/365* (2013.01); *A45D 7/04* (2013.01); *A61K 8/362* (2013.01); *A61Q 5/06* (2013.01); *A61K 2800/884* (2013.01)

(58) Field of Classification Search
None
See application file for complete search history.

(56) References Cited

U.S. PATENT DOCUMENTS

| 3,025,218 | A | 3/1962 | Strain |
| 3,470,887 | A | 10/1969 | Kremer |
| 3,482,581 | A | 12/1969 | Weigand |
| 3,805,809 | A | 4/1974 | Zeffren |
| 4,192,863 | A | 3/1980 | Kondo |
| 4,349,537 | A | 9/1982 | Forbriger, Jr. |
| 4,409,204 | A | 10/1983 | Lang |
| 4,911,919 | A * | 3/1990 | Patel ............... A61K 8/416 424/125 |
| 5,002,761 | A | 3/1991 | Mueller |
| 5,015,470 | A | 5/1991 | Gibson |
| 5,254,336 | A | 10/1993 | Hoshowski |
| 5,635,168 | A | 6/1997 | Burns |
| 5,655,552 | A | 8/1997 | Samain |
| 6,482,808 | B1 | 11/2002 | Springob et al. |
| 6,517,822 | B1 | 2/2003 | Buck |
| 6,723,308 | B2 | 4/2004 | Browning |
| 7,744,859 | B2 | 6/2010 | Campain |
| 7,988,954 | B2 | 8/2011 | Chandra |
| 8,192,730 | B2 | 6/2012 | Elliott |
| 8,324,183 | B2 | 12/2012 | Kawano |
| 2001/0007160 | A1 | 7/2001 | Yamaguchi et al. |
| 2003/0021758 | A1 | 1/2003 | Cannell |
| 2003/0108505 | A1 | 6/2003 | Cao |
| 2005/0214238 | A1 | 9/2005 | Fukuhara |
| 2006/0096042 | A1 | 5/2006 | Schonert |
| 2006/0272107 | A1 | 12/2006 | Malle et al. |
| 2007/0298003 | A1 | 12/2007 | Chandra |
| 2008/0019938 | A1 | 1/2008 | Elliott |
| 2008/0019939 | A1 | 1/2008 | Verboom |
| 2009/0126756 | A1 | 5/2009 | Syed |
| 2009/0165812 | A1 | 7/2009 | Resnick |
| 2009/0252697 | A1 | 10/2009 | Barbarat |
| 2009/0320869 | A1 | 12/2009 | Fadeeva et al. |
| 2010/0172855 | A1* | 7/2010 | Paul ............... A61K 8/44 424/70.11 |
| 2010/0196303 | A1 | 8/2010 | Paul |
| 2010/0202994 | A1 | 8/2010 | Kasai |
| 2010/0233114 | A1* | 9/2010 | DeGeorge ............... A61K 8/585 424/70.121 |
| 2010/0300471 | A1 | 12/2010 | Malle |
| 2010/0307525 | A1* | 12/2010 | De Boni ................... A45D 7/06 132/206 |
| 2011/0052520 | A1 | 3/2011 | Nguyen et al. |
| 2011/0256084 | A1 | 10/2011 | Dixon |

(Continued)

FOREIGN PATENT DOCUMENTS

| CN | 1679481 | 10/2005 |
| DE | 2438534 | 2/1976 |

(Continued)

OTHER PUBLICATIONS

Co-pending Application: Applicant: Murray et al., U.S. Appl. No. 15/036,445, filed May 13, 2016.
Co-pending Application: Applicant: Iftikhar et al., U.S. Appl. No. 15/036,425, filed May 13, 2016.
Barclay-Nichols, Thickeners: Cationic guar gum, Swift Crafty Monkey Blogspot, 2011, pp. 1-14; http://swiftcraftymonkey.blogspot.com/2011/02/thickeners-cationic-guar-gum.html.
Nature's Aid, "What You Need to Know About Guar Hydroxypropyltrimonium Chloride", 2015, pp. 1-4; http://www.naturesaid.ca/about-guar-hydroxypropyltrimonium-chloride/.

(Continued)

*Primary Examiner* — Jyothsna A Venkat
(74) *Attorney, Agent, or Firm* — Foley & Lardner LLP

(57) ABSTRACT

A method for styling hair comprising: —applying to hair a hair treatment composition comprising from 4 to 25 wt % a citric or aconitic acid and having a pH of from 1 to 3; —leaving the product on the hair for from 5 to 90 minutes; —rinsing the product from the hair; and —styling.

6 Claims, No Drawings

(56) References Cited

U.S. PATENT DOCUMENTS

| | | |
|---|---|---|
| 2012/0093757 A1 | 4/2012 | Murray et al. |
| 2012/0192888 A1 | 8/2012 | Philippe |
| 2012/0312317 A1 | 12/2012 | Mannozzi |
| 2015/0128984 A1 | 5/2015 | Paul |
| 2015/0136167 A1 | 5/2015 | Murray |
| 2015/0328119 A1 | 11/2015 | Paul |

FOREIGN PATENT DOCUMENTS

| | | |
|---|---|---|
| DE | 4300320 | 7/1994 |
| EP | 1066019 | 1/2001 |
| EP | 1174111 | 1/2002 |
| EP | 1174112 | 1/2002 |
| EP | 1393708 | 3/2004 |
| EP | 1428497 | 6/2004 |
| EP | 1579843 | 9/2005 |
| EP | 1634570 | 3/2006 |
| EP | 1719545 | 11/2006 |
| FR | 2721823 | 1/1996 |
| FR | 2929508 | 10/2009 |
| JP | 6298629 | 10/1994 |
| JP | 2005272377 | 10/2005 |
| JP | 2005533085 | 11/2005 |
| JP | 2006182702 | 7/2006 |
| JP | 2009519272 | 5/2009 |
| JP | 2010159254 | 7/2010 |
| JP | 2013514264 | 4/2013 |
| JP | 2007505819 | 3/2018 |
| WO | WO9405754 | 3/1994 |
| WO | WO03039497 A1 | 5/2003 |
| WO | WO2004004672 | 1/2004 |
| WO | WO2005025524 | 3/2005 |
| WO | WO2005084622 | 9/2005 |
| WO | WO2005084623 | 9/2005 |
| WO | WO2007068400 | 6/2007 |
| WO | WO2008132101 | 11/2008 |
| WO | WO2009003808 | 1/2009 |
| WO | WO2009047251 | 4/2009 |
| WO | WO2009138288 A1 | 11/2009 |
| WO | WO2010001632 | 1/2010 |
| WO | WO2010049434 A2 | 5/2010 |
| WO | WO2010141098 | 12/2010 |
| WO | WO2011074143 | 6/2011 |
| WO | WO2012084532 | 6/2012 |
| WO | WO2012084533 | 6/2012 |
| WO | WO2012122457 | 9/2012 |
| WO | WO2013/174575 | * 11/2013 |
| WO | WO2013174575 | 11/2013 |

OTHER PUBLICATIONS

IPRP2 in PCTEP2014074677 dated Dec. 1, 2015. pp. 1 to 9.
IPRP2 in PCTEP2014074998 dated Jan. 15, 2016. pp. 10 to 23.
IPRP2 in PCTEP2014074999 dated Feb. 9, 2016. pp. 24 to 34.
IPRP2 in PCTEP2014075000 dated Jun. 22, 2015. pp. 35 to 47.
Search Report and Written Opinion in EP13193932 dated Feb. 27, 2014. pp. 1 to 6.
Search Report and Written Opinion in EP13193933 dated Apr. 23, 2014. pp. 7 to 16.
Search Report and Written Opinion in EP13193934 dated Apr. 24, 2014. pp. 17 to 23.
Search Report and Written Opinion in EP13193935 dated Apr. 23, 2014. pp. 24 to 29.
Search Report and Written Opinion in PCTEP2013057809 dated Jul. 17, 2013. pp. 1 to 12.
Search Report and Written Opinion in PCTEP2014074677 dated Jan. 21, 2015. pp. 13 to 21.
Search Report and Written Opinion in PCTEP2014074999 dated Feb. 26, 2015. pp. 22 to 38.
Search Report and Written Opinion in PCTEP2014075000 dated Jun. 22, 2015. pp. 39 to 50.
Search Report and Written Opinions in PCTEP2014074998 dated Jun. 19, 2015. pp. 51 to 69.
Co-pending Application: Applicant: Murray et al., U.S. Appl. No. 14/400,965, filed Nov. 13, 2014.
Written Opinion in EP13715708 dated Nov. 2, 2016.
Opposition notice in EP137157085; dated Jan. 14, 2019.
Search Report & Written Opinon in BR112014028727-9, dated Sep. 15, 2005, Unilever PLC et al.

* cited by examiner

METHOD OF TREATING HAIR

The invention relates to a method of hair styling.

Permanent hair straightening compositions that are on the market are based on chemical treatment of the hair in a two-step process using thiol- or hydroxide-based reducing agents followed by a neutralisation or oxidation step. Such systems have various negatives associated with them; in that the process itself is difficult to conduct, in many instances this straightening process is undertaken by a qualified hairdresser in a professional salon. Furthermore the straightening process damages the hair, has an unpleasant odor and can cause irritation to the scalp.

Surprisingly we have found that hair can be styled without causing damage, without using hair irons and the hair remains styled even after subsequent washing.

Accordingly, the present invention provides a method according to claim 1.

Preferably the present invention provides a method for styling hair comprising the following sequential steps:
1) applying to hair a hair treatment composition comprising from 4 to 25 wt % a citric or aconitic acid and having a pH of from 1 to 3;
2) leaving the product on the hair for from 5 to 90 minutes;
3) rinsing the product from the hair; and
4) styling.

Preferably the pH of the composition is 1 to 3, more preferably from 1.0 to 3.0.

The total level of citric or aconitic acid is from 2-25% wt. of the total hair treatment composition, more preferably from 3-20 wt % and most preferably 4-8 wt %.

The hair treatment compositions used in the present invention can comprise a carrier, or a mixture of such carriers, which are suitable for application to the hair. The carriers are present at from about 0.5% to about 95%, preferably from about 5.0% to about 90%, more preferably from about 10.0% to about 90.0%, of the composition.

By 'dry hair' is meant that the amount of free water disposed on the cuticle has been substantially removed by towelling or evaporation such that it constitutes no more than 25% wt. of the hair fibre as a whole.

This means that the hair has not been washed or actively wetted, such as by shampooing, conditioning, rinsing or otherwise treating with an aqueous composition in the preceding 2, preferably 3 hours and has been permitted to acclimatise to atmospheric conditions.

In such circumstances there is substantially no free water on the hair fibre which interferes with the adsorption of the hair treatment composition on application.

By aqueous composition is meant that the compositions of the invention comprise 60% by weight or more of water, preferably 70% or more, more preferably 80% or more. Preferably, such a composition used in the present invention comprises less than 95% wt. and more preferably less than 90% wt. water.

Preferably, the hair treatment composition used in accordance with the invention includes conditioning materials. Preferred conditioning materials include cationic surfactants, silicones, fatty alcohols and mixtures thereof.

Preferably, the composition of the invention comprises a cationic surfactant.

Preferably, the cationic surfactant has the formula $N^+R^1R^2R^3R^4$ wherein $R^1$, $R^2$, $R^3$ and $R^4$ are independently ($C_1$ to $C_{30}$) alkyl or benzyl. Preferably, one, two or three of $R^1$, $R^2$, $R^3$ and $R^4$ are independently ($C_4$ to $C_{30}$) alkyl and the other $R^1$, $R^2$, $R^3$ and $R^4$ group or groups are ($C_1$-$C_6$) alkyl or benzyl. More preferably, one or two of $R^1$, $R^2$, $R^3$ and $R^4$ are independently ($C_6$ to $C_{30}$) alkyl and the other $R^1$, $R^2$, $R^3$ and $R^4$ groups are ($C_1$-$C_6$) alkyl or benzyl groups. Optionally, the alkyl groups may comprise one or more ester (—OCO— or —COO—) and/or ether (—O—) linkages within the alkyl chain. Alkyl groups may optionally be substituted with one or more hydroxyl groups. Alkyl groups may be straight chain or branched and, for alkyl groups having 3 or more carbon atoms, cyclic. The alkyl groups may be saturated or may contain one or more carbon-carbon double bonds (e.g. (e.g. oleyl).

Alkyl groups are optionally ethoxylated on the alkyl chain with one or more ethyleneoxy groups.

Suitable cationic surfactants for use in conditioner compositions according to the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, dihydrogenated tallow dimethyl ammonium chloride (eg, Arquad 2HT/75 from Akzo Nobel), cocotrimethylammonium chloride, PEG-2-oleammonium chloride and the corresponding hydroxides thereof. Mixtures of any of the foregoing materials may also be suitable. A particularly useful cationic surfactant for use in conditioners according to the invention is cetyltrimethylammonium chloride, available commercially, for example as GENAMIN CTAC, ex Hoechst Celanese. Another particularly useful cationic surfactant for use in conditioners according to the invention is behenyltrimethylammonium chloride, available commercially, for example as GENAMIN KDMP, ex Clariant.

Preferably present at from 0.01 to 10% wt., more preferably from 0.05 to 7.5% wt. and most preferably from 0.1 to 5% of the treatment composition for use in the method of the invention.

Preferably, the treatment composition for use in the method of the invention comprises from 0 to 0.1% wt. and is more preferably free from an amidoamine corresponding to the general formula (I):

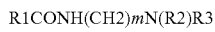

in which $R^1$ is a hydrocarbyl chain having 10 or more carbon atoms, $R^2$ and $R^3$ are independently selected from hydrocarbyl chains of from 1 to 10 carbon atoms, and m is an integer from 1 to about 10; and Notable amidoamines include stearamido-propyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethyl-amine, behenamidopropyldiethylmine, behenamidoethyldiethyl-amine, behenamidoethyldimethylamine, arachidamidopropyldimethylamine, arachidamidopropyldiethylamine, arachid-amidoethyldiethylamine, arachidamidoethyldimethylamine, and mixtures thereof.

Such amidoamines are typically included with an acid which protonises the amine to form a cationic surfactant.

In accordance with the method of the invention the treatment composition is applied to the hair and left for at least 5 minutes, preferably at least 10 minutes, more preferably at least 15 minutes and most preferably at least 20 minutes before being rinsed off.

Preferably the product is rinsed off 90 minutes after application, more preferably 60 minutes and most preferably 40 minutes after application.

Preferably, the method is conducted without the addition of heat in the form of hair straighteners or irons. Accordingly, the method is conducted at from 15 to 45 C, more preferably from 20 to 30 C.

The following non-limiting examples further illustrate the preferred embodiments of the invention. All percentages referred to in the examples and throughout this specification are by weight based on total weight unless otherwise indicated.

EXAMPLE 1

To demonstrate the straightening benefit of citric acid as a function of pH.

Dark brown European wavy #6 switches of length 25 cm and weight 2 g, were dosed with 2 ml each of 5% citric acid solutions at various pH's. They were combed straight and left to dry 20 minutes. They were subsequently rinsed for 30 seconds under the tap. They were then combed straight and left to dry overnight. When dry, the switches were combed straight and images taken. The volume of the switches shows the straightening benefit of citric acid. Volume refers to the projection of the switch image onto the screen and is given in mm$^2$.

| Treatment | Volume in mm$^2$ | % benefit over water |
| --- | --- | --- |
| water | 14278 | 0 |
| 5% citric acid at pH 2 | 9481 | 33.6 |
| 5% citric acid at pH 3 | 9574 | 32.9 |
| 5% citric acid at pH 4 | 11717 | 17.9 |
| 5% citric acid at pH 5 | 10871 | 23.9 |
| 5% citric acid at pH 6 | 12136 | 15.0 |

From the table it can be seen that the straightening benefit for citric acid is achieved only at low pH.

EXAMPLE 2

In this experiment the effect of re-wetting some of the switches above is investigated. Switches from Example 1 were re-wetted, combed straight and left to dry. When dry the switches were combed and images recorded.

| Treatment | Volume in mm$^2$ | % benefit over water |
| --- | --- | --- |
| water | 14081 | 0 |
| 5% citric acid at pH 2 | 10205 | 27.5 |
| 5% citric acid at pH 4 | 11509 | 18.3 |

The table above shows that the straightness benefit is maintained even after re-wetting. This illustrates that the style supported by a composition with citric acid is durable over time and is not immediately washed out when the hair is next cleansed.

The invention claimed is:

1. A method for styling hair consisting of:
    i) applying to dry hair an aqueous hair treatment composition consisting of from 4 to 25 wt % citric acid and having a pH of from 1 to 3;
    ii) leaving the hair treatment composition on the hair for from 5 to 90 minutes;
    iii) rinsing the hair treatment composition from the hair; and
    iv) styling.

2. The method according to claim 1 in which the composition is left on the hair for at least 5 minutes 20 minutes.

3. The method according to claim 1 in which the level of citric acid is from 8 to 20 wt % of the total composition.

4. The method according to claim 1 wherein styling constitutes straightening, providing body or retaining curl.

5. The method according to claim 1 for durably styling the hair.

6. The method for durably styling the hair consisting of:
    i) applying to dry hair an aqueous hair treatment composition consisting of from 4 to 25 wt % citric acid and having a pH of from 1 to 3;
    ii) shampooing the hair after the application of the hair treatment composition; and
    iii) styling.

* * * * *